United States Patent [19]

Siegmeier et al.

[11] Patent Number: 4,801,759
[45] Date of Patent: Jan. 31, 1989

[54] PROCESS FOR PRODUCING VICINAL DIOLS

[75] Inventors: Rainer Siegmeier, Bad Homburg; Güther Prescher, Hanau; Helmut Maurer, Rodenbach, all of Fed. Rep. of Germany

[73] Assignee: Degussa Aktiengesellschaft, Frankfurt am Main, Fed. Rep. of Germany

[21] Appl. No.: 82,569

[22] Filed: Aug. 7, 1987

[30] Foreign Application Priority Data

Aug. 23, 1986 [DE] Fed. Rep. of Germany ....... 3628665

[51] Int. Cl.$^4$ .................................. C07C 29/10/31/20
[52] U.S. Cl. .................................. 568/833; 568/832; 568/838; 568/857; 568/866; 568/867
[58] Field of Search ............... 568/867, 866, 865, 857, 568/832, 833, 838

[56] References Cited

U.S. PATENT DOCUMENTS

| | | | |
|---|---|---|---|
| 1,641,710 | 9/1927 | Untiedt | 568/867 |
| 1,875,312 | 8/1932 | Youtz | 568/867 |
| 2,255,411 | 9/1941 | Cohen et al. | 568/867 |
| 2,472,417 | 6/1949 | Conze | 568/867 |
| 3,576,890 | 9/1971 | Binning | 568/867 |
| 4,112,054 | 9/1978 | Feingold et al. | 568/867 |
| 4,605,795 | 8/1986 | Siegmeier et al. | 568/867 |
| 4,626,603 | 12/1986 | Siegmeier et al. | 568/833 |

FOREIGN PATENT DOCUMENTS 0062234 4/1982 Japan .................................. 568/867

Primary Examiner—Werren B. Lone
Attorney, Agent, or Firm—Cushman, Darby & Cushman

[57] ABSTRACT

A method for the continuous saponification of epoxides with 3-8 carbon atoms at low pressures, preferably atmospheric pressure, and low boiling temperatures with small amounts of water. Yields and selectivities are very high.

12 Claims, 1 Drawing Sheet

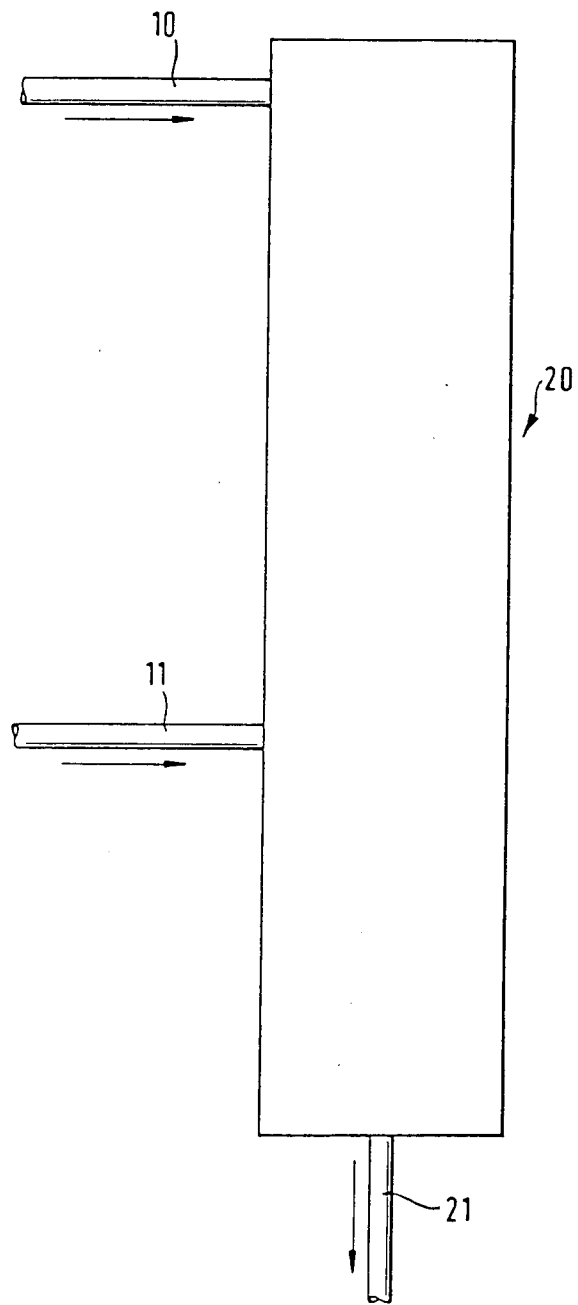

PROCESS FOR PRODUCING VICINAL DIOLS

The present invention relates to the production of certain vicinal diols by saponification of the corresponding epoxides in a purely aqueous medium.

BACKGROUND OF THE INVENTION

Vicinal diols are useful as components in the production of polyesters and polyurethanes as well as in the cosmetic and pharmaceutical industry. They are produced, inter alia, by the saponification of their corresponding epoxides. This saponification may be catalyzed both by the addition of acids (c.f., for example, the state of the art of U.S. Pat. No. 3,576,890) and of alkalis (c.f., for example, DE-OS No. 17 93 247; DE-OS No. 22 03 806) and of salts of aliphatic mono or polycarboxylic acids (DE-OS No. 22 56 907) as well as primary, secondary or tertiary amine salts or ammonium salts (EP-OS 0 025 961).

It is also known that the acid, acting as catalyst, can be produced by means of the addition of esters of lower carboxylic acids which are hydrolyzed to alcohol and acids (U.S. Pat. No. 3,576,890). The saponification can be performed in a purely aqueous medium or in the presence of solubilizing agents such as water-soluble ketones or cyclic ethers (DE-OS No. 22 56 907). A purely aqueous saponification without the presence of organic solvents or solubilizing agents is more advantageous, since it avoids the step of separating the solvents or solubilizing agents after the saponification has been completed.

According to Houben-Weyl, vol. VI/3, 1964, pp. 454–455, saponifications which last several hours at temperatures far above 100° C. and pressures of 12–20 bar are known which proceed without catalyst. In the presence of acid as catalyst, the saponification should proceed at "relatively low temperatures" and "rapidly"; more precise data is lacking.

However, according to a method described in "J. Am. Chem. Soc.", vol. 82, 1960, pp. 4328–29 (Korach) 2 hours are needed to produce cyclopentene diol by means of the saponification of epoxycyclopentene without the presence of a catalyst but in the presence of a solvent; the temperatures are set in two stages of 5°–10° C. at 15°–20° C. at an epoxide-water ratio of 1:12.

In the method of DE-AS 1 008 275, styrol oxide is saponified in the presence of an acidic catalyst such as sulfuric acid. However, the yields obtained are only approximately 80%.

DE-PS No. 34 42 938 teaches a continuous saponification of short chain epoxides in the presence of organic solvents with very good yields. This method includes the use of an organic solvent which is introduced e.g. from the epoxidation step of the epoxides used as starting materials.

SUMMARY OF THE INVENTION

The present invention has the object of efficiently performing a continuous saponification of aliphatic epoxides which contain 3 to 8 carbon atoms or cycloaliphatic epoxides to the corresponding diols in aqueous medium at low pressures.

In accordance with the present invention, it has been found that aliphatic linear or branched or cycloaliphatic diols can be obtained in very good yields and with excellent selectivity in a simple manner by saponifying aliphatic linear or branched epoxides containing 3 to 8 carbon atoms or cycloaliphatic epoxides with water at pressures of 1–5 bar under the boiling temperatures which develop. Organic solvents are not necessary for the process.

An acidic catalyst can be present if necessary.

BRIEF DESCRIPTION OF FIGURES OF DRAWING

FIG. 1 illustrates schematically an apparatus for carrying out the method of the invention.

DETAILED DESCRIPTION OF PREFERRED EMBODIMENTS

Aliphatic linear or branched epoxides containing 3 to 8 C atoms or cyclic epoxides which can be used in accordance with the present invention include the following: propylene oxide; 2,3-epoxypropanol-1; 1,2-butene oxide; 2,3-butene oxide; 3,4-epoxybutene-1; 1,2,3,4-butadiene dioxide; 2,3-epoxybutane-diol-1,4; 1,2-epoxy-2-methyl-butane; 2-pentene oxide; cyclopentene oxide; 2-methyl-1-butene oxide; 3-methyl-1-butene oxide; 2-methyl-2-butene oxide; 2,3-dimethyl-1-butene oxide; 1-hexene oxide; 2-hexene oxide; 3-hexene oxide; cyclohexene oxide; 4-methylpentene oxide; 5,6-epoxyhexene-1; 1,2,5,6-diepoxyhexane; 2,3,5,6-diepoxybicyclo-2,2,1-heptane; 2,3-epoxybicyclo-2,2,1-heptane, 1-heptene oxide; 3-heptene oxide; cycloheptene oxide; 1-octene oxide; 7,8-epoxy-octene-1; 1,2,7,8-diepoxyoctane; cyclooctene oxide; 1,2-epoxy-cyclooctene-5; 1,2,5,6-diepoxycyclooctane; 1,2,3,4-diepoxycyclooctane; 3,4-epoxy-cyclooctanol; 2,3-epoxybicyclo-3,3,0-octane; vinyl cyclohexene oxide; vinyl cyclohexene dioxide.

The following have proven to be very useful: the epoxides of propylene, 1-pentene, isoamylene, 1-hexene, 1-neohexene; 2,3-dimethylbutene-2 or cyclohexene, especially, however, epoxides with 5–7 carbon atoms, that is, pentene oxide-1, isoamylene oxide, hexene oxide-1; 2,3-dimethylbutene-2-oxide, neohexene oxide-1 and also cyclohexene oxide.

The weight ratio of epoxide to water is between 1:0.5 to 1:5, preferably around 1:1.5 to 1:2.5.

"Acidic catalysts" which can be used include inorganic and organic acids and their acid reacting salts.

Mineral acids which may be used include: sulfuric acid, hydrochloric acid, orthophosphoric acid and perchloric acid. Sulfuric acid is preferable.

Among the organic acids, formic acid, acetic acid and propionic acid, isobutyric acid as well as toluene sulfonic acid and methane sulfonic acid are advantageous. Formic acid is preferable.

The inorganic or organic acids may be added in concentrations of 0.01 to 5% by weight in relation to the amount of water.

The saponification occurs at the boiling temperature which develops in the reaction system under the particular pressure selected.

The method may be continuously operated, e.g., by continuously adding the starting materials to a conventional distillation column at atmospheric pressure or at a slightly elevated pressure up to 5 bar. Both packed columns and plate columns can be used as saponification columns. Loop-type bubble reactors can also be used.

In these saponification columns, the epoxide to be saponified is added in the middle and the water, which can already contain an acidic catalyst, if one is used, is added near the top of the column.

The practice of the invention is illustrated in the drawing. In the apparatus illustrated in the drawing, the epoxide is introduced via line 11 into the middle of saponification column 20. Fresh water is added via line 10 at the top of the column. The water flowing in via line 10 can contain a catalyst if one is desired. The column is operated under total reflux; the epoxide is completely converted.

An acidic aqueous solution of the diol is removed from the bottom of column 20 via line 21. It is neutralized and freed of water, preferably by means of distillation. A further purification is usually unnecessary, but the product can be distilled.

The invention makes it possible to achieve a quantitative conversion of epoxide with small amounts of water (in relation to the epoxide) as well as low pressures, especially atmospheric pressure, and the low boiling temperatures which are possible at those pressures. The selectivities of the continuous method are very high and result, in all instances, in yields of diol above 90%. With the exception of propylene oxide, the yields are usually in the mid-ninety percent range, but usually they are higher. The formation of by-products is drastically reduced in relation to a discontinuous method.

Since the method can be performed in a traditional distillation column, it is extremely simple to perform.

Since the diols formed accumulate in relatively small amounts of water, only small amounts of water have to be distilled off, if it should be considered necessary to remove them.

The advantages of the invention, particularly as regards conversion, yield and formation of by-products will be more apparent from the following example, the results being listed in Table I for the continuous method of the invention and in Table II for the discontinuous method according to the state of the art.

EXAMPLE 1

The starting materials (epoxide, water and sulfuric acid) were introduced into a column. The column was operated under atmospheric pressure (1 bar) and at the boiling temperature which developed thereby.

The epoxide was introduced as illustrated in FIG. 1 via line 11 into column 20, the indicated amounts of water, which—except for test 6—contained the acidic catalyst in the amount indicated, entered the column via line 10. The saponification time was between 1.4 to 1.6 hours, by which time a quantitative epoxide conversion was achieved.

Titrimetic analysis demonstrated the absence of epoxide in the bottom product. The amount of the diol formed and of the amounts of by-products was determined by gas chromatography.

EXAMPLE 2

Table II contains data derived from a discontinuous process according to the state of the art. These tests were performed as follows:

100 g of the indicated epoxide were mixed with 200 g water which contained the indicated amounts of concentrated sulfuric acid in a three-neck flask with agitator, inner thermometer and reflux condenser and heated at atmospheric pressure to boiling at the specified saponification times. The epoxide conversions were more than 99.7% at the indicated reaction times.

The conversions were determined titrimetrically and the amounts of diol and of by-products were determined by gas chromatography.

TABLE 1

Continuously Performed Tests - Example 1

| | Epoxide | Epoxide Addition g/h | Amount of Water g/h | Concentration of $H_2SO_4$ g-%* | Yield % | High-Boiling By-Products g/100 g diol | Product |
|---|---|---|---|---|---|---|---|
| 1. | Propylene oxide | 200 | 427 | 1 | 91.8 | 7.8 | Propanediol-1,2 |
| 2. | Pentene oxide-1 | 174 | 352 | 0.1 | 98.0 | 1.8 | Pentanediol-1,2 |
| 3. | Isoamylene oxide | 169 | 350 | 0.01 | 97.4 | 2.8 | 2-methyl-butanediol-2,3 |
| 4. | Hexene oxide-1 | 114 | 351 | 0.1 | 98.8 | 1.0 | Hexanediol-1,2 |
| 5. | Hexene oxide-1 | 243 | 351 | 0.2 | 97.4 | 2.4 | Hexanediol-1,2 |
| 6. | 2,3-dimethyl-butene-2-oxide | 177 | 351 | — | 99.7 | 0.3 | 2,3-dimethyl-butanediol-2,3 |
| 7. | Neohexene oxide-1 | 190 | 349 | 1.5 | 98.2 | 1.7 | Neohexanediol-1,2 |
| 8. | Cyclohexene oxide | 402 | 348 | 0.05 | 94.9 | 4.9 | Cyclohexanediol-1,2 |
| 9. | Cyclohexene oxide | 186 | 349 | 0.05 | 97.7 | 2.1 | Cyclohexanediol-1,2 |

*Sulfuric acid concentration in relation to the amount of water

TABLE II (Discontinuous Addition) - Example 2

| | Epoxide | Concentration of $H_2SO_4$ g-%* | Reaction Time hours | Yield (%) | High Boiling By-Products g/100 g Diol |
|---|---|---|---|---|---|
| 1. | Propylene oxide | 0.1 | 0.6 | 77 | 18.2 |
| 2. | Pentene oxide-1 | 0.1 | 0.3 | 87 | 7.4 |
| 3. | Hexene oxide-1 | 0.1 | 0.3 | 88 | 10.5 |
| 4. | Cyclohexene oxide | 0.1 | 0.2 | 94 | 3.5 |
| 5. | Neohexene oxide | 1.0 | 0.3 | 86 | 10.4 |
| 6. | Octene oxide-1 | 0.1 | 1.5 | 76 | 19.6 |

*Sulfuric Acid Concentration in relation to the amount of water

What is claimed is:

1. A continuous process for producing low molecular weight vicinal diols by saponification of the corresponding epoxides with water at low pressure and moderate temperatures, said process comprising continuously supplying water and an aliphatic linear or branched epoxide or a cycloaliphatic epoxide, said epoxide containing 3–8 carbon atoms, in a weight ratio of 1:0.5 to 1:2.5 to a reaction vessel in the absence of any organic solvent, heating the epoxide and water at a pressure of 1–5 bar, refluxing at the boiling temperatures which develop, and drawing off an aqeuous solution of the resulting diol.

2. A process according to claim 1 wherein the epoxide is selected from the group consisting of propylene oxide, 1-pentene oxide, isoamylene oxide, 1-hexene oxide, 1-neohexene oxide, 2,3-dimethylbutene-2 oxide and cyclohexene oxide.

3. A process according to claim 1, wherein the water which is supplied to the reaction vessel contains an acid catalyst.

4. A process according to claim 3 wherein the acid catalyst is a mineral acid.

5. A process according to claim 4 wherein the mineral acid is selected from the group consisting of sulfuric acid, hydrochloric acid, orthophosphoric acid and perchloric acid.

6. A process according to claim 5 wherein the acid is sulfuric acid.

7. A process according to claim 3 wherein the acid catalyst is an organic acid.

8. A process according to claim 7 wherein the organic acid is selected from the group consisting of formic acid, acetic acid, propionic acid, isobutyric acid, methane sulfonic acid and toluene sulfonic acid.

9. A process according to claim 8 wherein the organic acid is formic acid.

10. A process according to any one of claims 4–9, wherein the water contains the acid catalyst in an amount of 0.01 to 5% by weight.

11. A process according to claim 1, wherein the reaction vessel is a distillation column, the water is supplied at the top of the column, the epoxide is supplied at the middle of the column, and the aqueous solution of the resulting diol is drawn off at the bottom of the column.

12. A process according to claim 3, wherein the reaction vessel is a distillation column, the water is supplied at the top of the column, the epoxide is supplied at the middle of the column, and the aqueous solution of the resulting diol is drawn off at the bottom of the column.

* * * * *